(12) United States Patent
Eck et al.

(10) Patent No.: US 6,703,511 B2
(45) Date of Patent: Mar. 9, 2004

(54) METHOD FOR OBTAINING PURE N-VINYL PYRROLIDONE

(75) Inventors: Bernd Eck, Viernheim (DE); Jörg Heilek, Bammental (DE); Martin Schmidt-Radde, Beindersheim (DE); Herbert Helfert, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/296,046

(22) PCT Filed: May 25, 2001

(86) PCT No.: PCT/EP01/06006

§ 371 (c)(1),
(2), (4) Date: Nov. 21, 2002

(87) PCT Pub. No.: WO01/90066

PCT Pub. Date: Nov. 29, 2001

(65) Prior Publication Data

US 2003/0166947 A1 Sep. 4, 2003

(30) Foreign Application Priority Data

May 26, 2000 (DE) .......................................... 100 26 233

(51) Int. Cl.$^7$ .......................................... C07D 207/267

(52) U.S. Cl. ....................................... 548/543; 548/555
(58) Field of Search ........................................... 548/543

(56) References Cited

U.S. PATENT DOCUMENTS

| 4,873,336 A | 10/1989 | Liu et al. ..................... 546/243 |
| 5,101,044 A | 3/1992 | Schuster et al. ............. 548/543 |
| 5,329,021 A | * 7/1994 | Cohen et al. ............. 548/543 |
| 5,508,396 A | 4/1996 | Steffen ........................ 540/451 |
| 5,710,284 A | 1/1998 | Schmidt-Radde et al. .. 548/543 |

FOREIGN PATENT DOCUMENTS

| DE | 3928982 | 3/1991 |
| EP | 767169 | 4/1997 |
| WO | 94/18166 | 8/1994 |

* cited by examiner

Primary Examiner—Flona T. Powers
(74) Attorney, Agent, or Firm—Keil & Weinkauf

(57) ABSTRACT

The invention describes a process for the isolation of pure N-vinylpyrrolidone from N-vinylpyrrolidone-containing crude products, comprising a single-stage or multistage crystallization process, which comprises passing the mother liquor from the first crystallization stage either to a distillative and/or extractive purification, or returning it to an N-vinylpyrrolidone-containing product stream of the preparation process.

8 Claims, 1 Drawing Sheet

METHOD FOR OBTAINING PURE N-VINYL PYRROLIDONE

Figure 1:
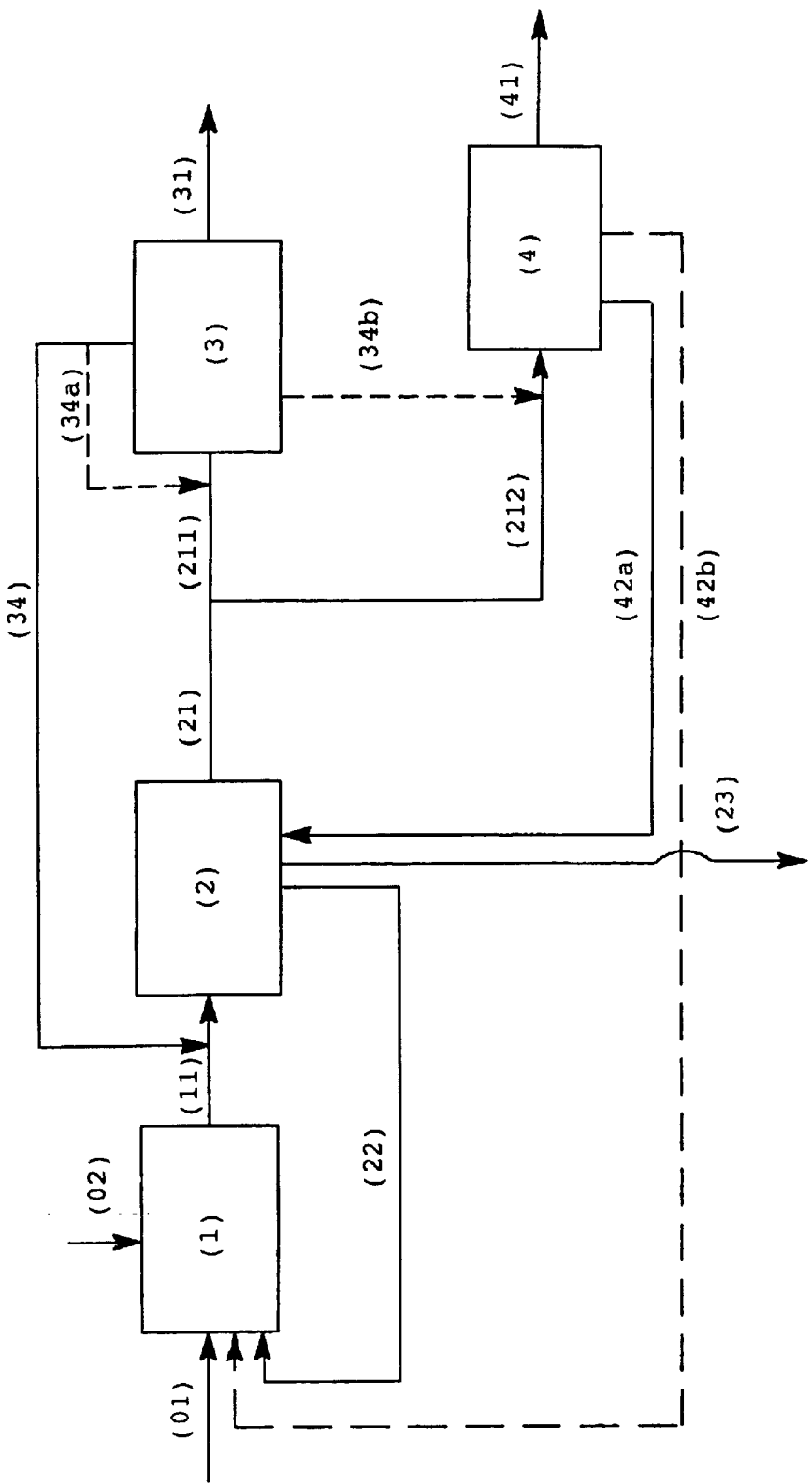

The present invention relates to a process for the isolation of pure N-vinylpyrrolidone from N-vinylpyrrolidone-containing crude products.

Homopolymers and copolymers of N-vinylpyrrolidone are used widely. They are often used as monomers for the preparation of polymers for cosmetic products, for the pharmaceutical sector and for food technology. For the last-named areas, high requirements are placed on the purity of the N-vinylpyrrolidone.

On an industrial scale, N-vinylpyrrolidone is prepared by vinylation of 2-pyrrolidone with acetylene under pressure in the presence of basic catalysts, such as hydroxides and alkoxides. The product obtained after distillation usually comprises the product of value in an amount of from 98 to 99.9%, the main impurity being 2-pyrrolidone. In addition, the product also comprises a small amount of nitrogen and vinyl ether compounds, which sometimes lead to product discolorations and to the production of an odor during the polymerization.

A large number of applications require an N-vinylpyrrolidone which comprises less than 0.1% by weight of impurities. In principle, such a degree of purity can be achieved by fractional distillation. Removal of the compounds which are responsible for the product discoloration observed during the polymerization is possible only with difficulty in this way. For this reason, the distillation is often combined with an extractive work-up. DE 37 36 603, for example, describes the removal of such impurities using ion exchangers.

WO 94/18166 discloses the purification of N-vinylpyrrolidone by a multistage, fractional crystallization. In this process, a supercooled melt of the N-vinylpyrrolidone is crystallized, the mother liquor is separated off, and the crystallizate is subjected to at least one further crystallization stage. The product of value is likewise isolated from the mother liquor by multistage fractional crystallization. The process known from WO 94/18166 is based on the countercurrent principle, where in each crystallization stage the crystallizate is separated off from the crystallization residue (mother liquor), the crystallizate is passed to the next higher crystallization stage, and the crystallization residue (mother liquor) is passed to the next lower crystallization stage. The expenditure on apparatus for a crystallization process of this type is naturally high. In addition, the process is time-consuming because of the large number of crystallization stages.

EP-A 767 169 likewise describes a crystallization process for the purification of N-vinylpyrrolidone, which differs from the process known from WO 94/18166 by virtue of the fact that instead of supercooling the melt, the crystallization of the N-vinylpyrrolidone is initiated at the crystallization temperature using seed crystals. Here too, the mother liquor from the first crystallization stage is worked up by one or more successive crystallization stages. Although, as a result of the greater efficiency, fewer crystallization stages are required than in the case of the process of WO 94/18166, the expenditure on apparatus is very high for this process as well.

It is an object of the present invention to provide a process for the isolation of pure N-vinylpyrrolidone from N-vinylpyrrolidone-containing crude products, which can be operated with low expenditure on apparatus and produces N-vinylpyrrolidone of high purity. Furthermore, the process should advantageously lend itself to being incorporated into a continuous process for the preparation of N-vinylpyrrolidone.

We have found that this object is achieved by a process for the isolation of pure N-vinylpyrrolidone from N-vinylpyrrolidone-containing crude products, comprising a single-stage or multistage crystallization process, which comprises passing the mother liquor from the first crystallization stage either to a distillative and/or extractive purification, or returning it to an N-vinylpyrrolidone-containing product stream of the preparation process.

The process according to the invention for purifying N-vinylpyrrolidone may, in principle, be incorporated either into a discontinuous process, or into a continuous process for the preparation of N-vinylpyrrolidone. It is particularly advantageous to incorporate the purification process according to the invention into a continuous preparation process for N-vinylpyrrolidone.

In the process according to the invention, the pure N-vinylpyrrolidone is isolated from the crude product by crystallization of the crude product, which may be carried out in a single stage or in two or more stages. The crystallization is of course carried out such that a separation into a crystalline, N-vinylpyrrolidone-enriched phase, and a liquid, N-vinylpyrrolidone-depleted phase (mother liquor) is obtained.

According to the invention, the mother liquor, formed during the crystallization, from the first crystallization stage, i.e. the crystallization stage into which the N-vinylpyrrilidone-containing crude product is fed, is not subjected to further crystallizing work-up. Instead, the mother liquor is worked up by, according to a first process variant, introducing it to an extractive and/or distillative purification, preferably a combined extractive and distillative purification.

Distillative purification here is understood as meaning a single-stage or multistage fractional distillation in which low-boiling components, i.e. compounds with a higher vapor pressure than N-vinylpyrrolidone, and high-boiling components, i.e. compounds with a lower vapor pressure than N-vinylpyrrolidone, in particular 2-pyrrolidone itself, are separated off from the mother liquor and from the product of value. Preferably, the distillative purification is carried out as vacuum distillation. The distillation temperatures are usually in the range from 50 to 150° C. and in particular in the range from 80 to 120° C. at a pressure of from 1 to 100 torr and in particular from 5 to 20 torr. The low-boiling components produced in the process, in particular 2-pyrrolidone-containing fractions, can be returned via the crude distillation or directly to the actual preparation process. The distillative purification is preferably combined with an extractive purification.

In a second variant of the process according to the invention, the mother liquor is returned to an N-vinylpyrrolidone-containing product stream of the preparation process. Where a crude distillation of the N-vinylpyrrolidone-containing product stream is intended, the mother liquor can be returned either to the product stream before the crude distillation or to the crude distillation, or to the product stream after the crude distillation. It is preferably returned to the product stream before the crude distillation. In both cases, it is advisable to remove from the system any low-boiling fractions in a dedicated fractionating distillation. This avoids a build up in the level of these components in the crude product.

It is of course also possible to combine the distillative/extractive work-up of the mother liquor according to process variant 1 with the return of the mother liquor to the preparation process, preferably before or into the crude distillation, according to process variant 2.

In a particularly preferred embodiment of the process according to the invention, the crude product to be purified is divided into two substreams T1 and T2. The substream T1 is passed to the crystallization. The substream T2 is subjected to distillative and/or extractive work-up, as described above.

The mother liquor produced in the crystallizing work-up can then, depending on the process variant, either be returned to an N-vinylpyrrolidone-containing product stream of the preparation process, as described above, or be passed to the substream T2. Via the substream T2, the mother liquor is then passed to the distillative and/or extractive work-up. This procedure firstly has the advantage that it is possible to prepare products of varying qualities in a targeted manner according to need and the requirements for the N-vinylpyrrolidone. Secondly, this procedure permits the simple incorporation of a process for the preparation of a high-purity N-vinylpyrrolidone by crystallization into an existing, continuous preparation process in which the purification is carried out by means of distillative and/or extractive steps. Furthermore, this process permits the simple incorporation of the mother liquor to be returned from the crystallization process to an existing distillative work-up concept. The laborious work-up of the mother liquor is dispensed with. Furthermore, some or all of the mother liquor can be returned to the stream T1.

The N-vinylpyrrolidone-containing crude product to be passed to the crystallization in the process according to the invention is not subject to any limitations. Preferably, the N-vinylpyrrolidone-containing crude product comprises not more than 20% by weight, preferably not more than 10% by weight and in particular 0.3 to 2% by weight, of 2-pyrrolidone and not more than 1% by weight and in particular not more than 0.1% by weight of low-boiling and/or color-imparting impurities. Such crude products are usually isolated by distillative work-up (crude distillation) of the product stream which forms during the preparation of the N-vinylpyrrolidone. The crude distillation is preferably carried out in the form of a vacuum distillation in which the product of value, N-vinylpyrrolidone, is distilled off overhead, and a large proportion of the 2-pyrrolidone is stripped off as bottom product. The latter is usually returned to the preparation process.

The actual crystallization of the N-vinylpyrrolidone-containing crude product can be carried out analogously to known crystallization processes. Suitable crystallization processes are known, for example, from U.S. Pat. No. 5,329,021, DE-A 26 06 364, DE-A 17 69 123 and EP-A 475 893. To carry out the crystallization, the crude product to be purified is usually transferred to a crystallizer and, with cooling of the crude product, some of the N-vinylpyrrolidone is crystallized out. The N-vinylpyrrolidone-containing mother liquor produced during the process is separated off and subjected to the measures given in claim 1. The crystallization is preferably continued until at least 5% by weight and preferably at least 20% by weight of the N-vinylpyrrolidone present in the crude product passed to the crystallization have crystallized out. As a rule, not more than 95% by weight, in particular not more than 80% by weight, of the N-vinylpyrrolidone present in the crude product will be crystallized out in order to achieve an adequate purification action.

The crystallizer used in the process according to the invention is not subject to any limitation. Particularly suitable crystallizers have proven to be those whose function is based on the formation of crystals on chilled surfaces. Crystallization processes of this type are also referred to as layer crystallization. Suitable apparatuses are described in DE-OS 17 69 123, DE-OS 26 06 364, EP-A 218 545, EP-A 323 377, CH 645278, FR 2668946 and U.S. Pat. No. 3,597,164.

For the layer crystallization, the crude product containing N-vinylpyrrolidone is brought into contact with the cooled surfaces of the heat exchanger. Here, the heat exchanger surfaces of the crystallizer are preferably cooled to temperatures up to 40 K below the melting temperature of the N-vinylpyrrolidone in the crude product. Upon reaching the desired degree of crystallization, the cooling operation is ended and the liquid mother liquor is discharged, e.g. by pumping off or flowing off. The purified, crystallized N-vinylpyrrolidone is usually isolated by heating the heat exchanger surfaces to a temperature above the melting point of the N-vinylpyrrolidone, the purified N-vinylpyrrolidone being produced as a melt and isolated as such. Where appropriate, further purification steps are carried out prior to isolation of the purified N-vinylpyrrolidone.

An additional purification step may be carried out, e. g. by sweating out of the crystal layer separated on the heat exchanger surfaces. To achieve this, the temperature of the crystal layer is slightly raised which leads to a melting of the more impure parts of the crystal layer and, thus, to an additional purification effect. Then, the sweat product is added to the mother liquor and further processed. It is also possible to treat the crystal layer with a purifying liquid, e. g. a melt of purified N-vinylpyrrolidone.

The temperature of the crude product in the crystallizer required for the layer crystallization depends on its composition. The upper limit is naturally the temperature at which the already crystallized N-vinylpyrrolidone is in equilibrium with the N-vinylpyrrolidone present in the mother liquor (equilibrium temperature). Depending on the composition of the crude product, the equilibrium temperature is in the range from +14.4 to –6° C. It is of course also possible to use lower temperatures for the crystallization. However, greatly supercooled melts are preferably avoided, so that the temperature of the crude product used for the crystallization is preferably not more than 5° C. and in particular not more than 2° C. below the equilibrium temperature. Typically, the temperature of the crude product during the layer crystallization is typically in the range from –10 to +14.4° C. and particularly preferably in the range from –5 to +14° C.

It has proven advantageous if the layer crystallization is carried out in the presence of seed crystals. The use of seed crystals during the crystallization of the N-vinylpyrrolidone is known in principle from EP-A 767 169, meaning that, in this regard, reference is made to this specification in its entirety. Here, a preferred procedure involves, prior to the crystallization, covering those surfaces of the crystallizer out of which crystals grow during the crystallization with a seed layer of N-vinylpyrrolidone. The seed crystals may be obtained either from the crude product to be purified or from a melt of purified N-vinylpyrrolidone. For example seed crystals can be generated on the surfaces of the crystallizer where the crystal growth is to take place by generating an N-vinylpyrrolidone-containing melt film on these surfaces and freezing the film on, for example by cooling to a temperature below the melting temperature. Preferably, the seed crystals are generated by applying a film from a suspension of N-vinylpyrrolidone crystals in an N-vinylpyrrolidone melt, and subsequently freezing this film on. The freezing-on is preferably carried out here at a temperature in the region of the equilibrium temperature.

A suspension of this type can be produced by freezing out a small amount of crystals from the crude product or a melt of the purified N-vinylpyrrolidone by supercooling. For example, crystals can be frozen out in scrape coolers or stirred tanks with close-clearance stirrers by indirect cooling from an N-vinylpyrrolidone-containing melt (crude product or melt of purified vinylpyrrolidone), which crystals are suspended in the melt using scraping elements on the cooled walls. It is also possible to generate the seed crystals directly in the melt by cooling the melt either via the crystallizer or via coolable elements (for example cold fingers or cooling sections) built in to the crystallizer to a temperature below the melting temperature. Seed crystals are preferably produced in an amount of from 0.1 to 700 g/kg of melt and in particular in the range of from 1 to 300 g/kg of melt.

In a preferred embodiment of the layer crystallization, the suspension is applied to the crystallizer surfaces by filling the crystallizer with the suspension and then emptying it. After emptying, a suspension layer remains on the crystallizer surfaces, which is then frozen on, preferably in the region of its equilibrium temperature.

The crystallization on cooling surfaces can then be carried out as a dynamic or static process. Preference is given to using the dynamic process. Static processes are described, for example in U.S. Pat. No. 3,597,164, EP 323 377 and FR 2668946, to which reference is hereby made. In the case of the static process, an exchange of materials in the liquid phase takes place only as a result of free convection (static melt).

In the case of the dynamic crystallization processes, the crude product to be crystallized is maintained in a flowing motion. This can be achieved by forced flow in heat exchangers with full flow-through, as described, for example in DE 26 06 364, or by the application of a trickling film to a cooled wall, as is described, for example, in DE-AS 1 769 123 and EP-A 218 545, or by means of agitated cooling surfaces such as cooling rolls or cooling belts. The dynamic layer crystallization is preferably carried out in heat exchangers with full flow-through, for example in externally cooled tubes or tube bundles.

In the case of the dynamic layer crystallization processes, in particular those which are carried out in heat exchangers with full flow-through, the procedure usually involves, optionally after applying the seed crystal layer to the heat exchanger surfaces of the crystallizer, bringing the N-vinylpyrrolidone-containing crude product into contact with the cooled heat exchanger surfaces, for example by allowing the crude product to flow through the cooled tubes of the crystallizer.

During this operation, the N-vinylpyrrolidone at least partially crystallizes out of the crude product. This operation is usually terminated when, because of the amount of N-vinylpyrrolidone which is crystallized out, an adequate through-flow of the melt through the heat exchanger is only just possible. For this purpose, the liquid phase (mother liquor) is removed and then the crystallized N-vinylpyrrolidone is isolated in the manner described above by, optionally after a further purification step, heating the heat exchanger surfaces to a temperature above the melting temperature of the N-vinylpyrrolidone. This operation can be repeated a number of times until the desired amount of N-vinylpyrrolidone has crystallized out from the crude product.

As an alternative to the layer crystallization, the crystallization can also be carried out as suspension crystallization. In the case of a suspension crystallization, individual crystals are formed in the liquid crude product containing N-vinylpyrrolidone by dissipating heat in the material. The crystal suspension which forms is agitated during the suspension crystallization process, for which purpose recirculation or stirring, in particular, are suitable. Adherence of crystals to heat exchanger surfaces is not required here and is even undesirable. Suspension crystallization is naturally a type of dynamic crystallization process since the crude product is agitated during crystallization. With regard to the temperatures of the crude product required for the crystallization of the N-vinylpyrrolidone, that which is stated above applies.

In the suspension crystallization, the heat is usually dissipated by indirect cooling, for example via scrape coolers connected to a stirred tank or a container without stirrer. The circulation of the crystal suspension is ensured here by a pump. However, it is also possible to dissipate the heat via the walls of the stirred tank with close-clearance stirrers. Also suitable for dissipating the heat is the use of cooling-disk crystallizers, as manufactured, for example, by GMF (Gouda in the Netherlands). The heat can of course also be dissipated by cooling via conventional heat exchangers (preferably tube-bundle or plate-type heat exchangers). However, in contrast to the abovementioned measures for the dissipation of heat, these apparatuses lead to the formation of crystal layers on the heat-exchanging surfaces. If, during operation, a state is achieved in which the heat transfer resistance assumes too high a value as a result of encrustation, a switch is made to a second heat exchanger. During the operating period of the second heat exchanger, the first exchanger is then regenerated, for example by melting off the crystal layer. If then too high a heat transfer resistance is reached in the second heat exchanger, then a switch back to the first heat exchanger is made. This measure can also be operated in rotation with more than two heat exchangers. The heat can also be dissipated by conventional partial evaporation of the crude product under reduced pressure.

The crystallizate enriched with N-vinylpyrrolidone which is produced during the suspension crystallization is separated from the depleted mother liquor by the processes of solid-liquid separation known for this purpose, for example by filtration, sedimentation and/or centrifugation. If the crystallizate is stationary, the mother liquor can also be removed by allowing it to run off. In the case of filtration, sedimentation or centrifugation, a preliminary thickening of the suspension is preferably carried out beforehand, for example by means of hydrocyclones. For the centrifugation, all known centrifuges which operate discontinuously or continuously are suitable. It is particularly advantageous to use push-air centrifuges which can be operated in a single stage or in two or more stages. Also suitable are screw screen centrifuges or screw discharge centrifuges (decanters). The filtration is usually carried out using suction filters which are operated continuously or discontinuously, with or without stirrer, or using belt filters. The filtration can be carried out at superatmospheric pressure or under reduced pressure.

The solid-liquid separation may be accompanied and/or followed by further process steps for increasing the purity of the crystals or of the crystal cake. Preferably, the removal of the crystals from the mother liquor is followed by a single-stage or multistage washing and/or sweating of the crystals or of the crystal cake. The wash liquid preferably used is liquid N-vinylpyrrolidone whose purity is above that of the mother liquor. The washing can be carried out in the apparatuses customary for this purpose, for example in centrifuges or in suction filters or belt filters. The washing can be carried out in a single stage or in two or more stages, the wash liquid preferably being conveyed in countercurrent relative to the crystal cake. In the case of a multistage crystallization, the wash liquid for the crystallizate of a particular crystallization stage is, in a particularly suitable manner, the feed to the same crystallization stage. The quantitative ratio of wash liquid to crystallizate is preferably in the range from 0.1 to 1, particularly preferably in the range from 0.2 to 0.6 kg of wash liquid to kg of crystallizate.

Particlarly preferably, a purification of the crystallizate is carried out during the suspension crystallization by carrying out the above-described washing, in particular on centrifuges or belt filters. It is of course also possible to combine washing and sweating operations in one apparatus.

To purify the crystallizate produced during the suspension crystallization, preference is given to using washing columns in which the crystallizate, usually following a prethickening e.g. by filtration or sedimentation, is passed in countercurrent to a washing liquid, it being possible to carry out the operation continuously or discontinuously. The wash liquid used is preferably a melt of the already purified crystallizate. Conveyance of the crystals against the direction of flow can be carried out in a customary manner, e.g. using gravitational force, preferably by mechanical conveyance or by hydraulic forces (e.g. flowing pressure losses upon flowing through the crystal pile).

All of the abovementioned crystallization processes can be carried out continuously or discontinuously.

The preferred dynamic layer crystallization is preferably carried out discontinuously, particularly if it is carried out in heat exchangers with full flow-through, as described above. Incorporation into a continuous preparation process is, however, directly possible, for example using containers for the intermediate storage of the crude product or by changing the ratio of substreams T1 and T2.

The purified N-vinylpyrrolidone obtained in the first crystallization stage can, if desired, be subjected to further crystallization stages, as are described, for example, in EP-A 767 169. In this respect, reference is made to the disclosure in this specification.

The purified N-vinylpyrrolidone produced during the crystallization generally comprises less than 0.7% by weight, in particular less than 0.1% by weight and particularly preferably less than 0.05% by weight, of impurities. The N-vinylpyrrolidone obtained in this way satisfies the requirements in the food industry or in the pharmaceutical sector.

FIG. 1 shows diagrammatically the incorportion of the crystallization according to the invention into an existing continuous preparation process for N-vinylpyrrolidone with distillative work-up:

2-Pyrrolidone (stream 01) and acetylene (stream 02) are reacted in the presence of a catalyst, e.g. an alkali metal hydroxide, in a reactor (1) under superatmospheric pressure, e.g. 10 to 25 bar, at elevated temperature, e.g. 145 to 170° C. The N-vinylpyrrolidone-containing product stream obtained during the process is separated by means of distillation (2) into a 2-pyrrolidone-containing fraction (22), into a high-boiling fraction (23) and into an N-vinylpyrrolidone-containing crude product (21). (22) is returned to the preparation process (1). The N-vinylpyrrolidone-containing crude product (21) is divided into a substream (211) and a substream (212). Substream (211) is subjected to a crystallization in a crystallizer (3), and separated into a product (31) purified by crystallization and the mother liquor. In one embodiment of the process, the mother liquor is returned to the preparation process, preferably before the distillation (2) (stream 34) and/or before the crystallization (3) (stream 34*a*)). In another embodiment, the mother liquor can be combined with the substream (212) and passed to a distillative/extractive work-up (4) (stream 34*b*). This gives a 2-pyrrolidone-containing fraction, some or all of which is passed to the distillation (2) (stream 42*a*)) and/or to the preparation (1) (stream 42*b*)), and also pure N-vinylpyrrolidone (41). The two processing variants for the mother liquor can be carried out in parallel (e.g. stream (34) and (34*b*)).

Using a process according to the invention it is possible, in a simple manner, to obtain N-vinylpyrrolidone in two product grades, it being possible to match the quantitative ratios to requirements in a simple manner via the substream quantitative ratios T1/T2. The N-vinylpyrrolidone which forms during the crystallization usually comprises less than 0.1% by weight of impurities. Multistage crystallization can give product grades with impurities of less than 100 ppm. Distillative work-up produces product grades having impurities of less than 0.5% by weight, in particular less than 0.1% by weight.

We claim:

1. A process for the isolation of pure N-vinylpyrrolidone from N-vinylpyrrolidone-containing crude products, comprising a single-stage or multistage crystallization process, which comprises passing the mother liquor from the first crystallization stage either to a distillative and/or extractive purification, or returning it to an N-vinylpyrrolidone-containing product stream of the preparation process.

2. A process as claimed in claim 1, wherein the N-vinylpyrrolidone-containing crude product is divided into two substreams T1 and T2, substream T1 being passed to a crystallization, and substream T2 being passed to an extractive and/or distillative purification.

3. A process as claimed in claim 2, wherein the mother liquor from the first crystallization stage is passed to the substream T2.

4. A process as claimed in claim 1, wherein an N-vinylpyrrolidone-containing crude product is used which has been obtained by distillative purification (crude distillation) of the N-vinylpyrrolidone-containing product stream of the preparation process.

5. A process as claimed in claim 4, wherein the mother liquor from the first distillation stage is returned, prior to the crude distillation, to the N-vinylpyrrolidone-containing product stream.

6. A process as claimed in claim 1, wherein the crystallization is carried out in a single stage.

7. A process as claimed in claim 6, wherein the crystallization is carried out up to a degree of crystallization in the range from 5 to 95%.

8. A process as claimed in claim 1, wherein the crystallization is carried out in the presence of seed crystals of N-vinylpyrrolidone.

* * * * *